United States Patent [19]

Ichikawa et al.

[11] 4,164,518

[45] Aug. 14, 1979

[54] PROCESS FOR PRODUCING DIPHENYLS

[75] Inventors: Yataro Ichikawa; Teizo Yamaji, both of Iwakuni, Japan

[73] Assignee: Teijin Limited, Osaka, Japan

[21] Appl. No.: 842,312

[22] Filed: Oct. 14, 1977

Related U.S. Application Data

[63] Continuation of Ser. No. 326,454, Jan. 24, 1973, abandoned, which is a continuation-in-part of Ser. No. 60,945, Aug. 4, 1970, abandoned.

[30] Foreign Application Priority Data

Apr. 4, 1969 [JP] Japan ..................... 44/26046

[51] Int. Cl.² .............. C07C 15/14; C07C 25/18; C07C 43/20
[52] U.S. Cl. ................ 585/427; 260/649 DP; 568/642
[58] Field of Search ............ 260/613 R, 670, 649 DP; 568/642

[56] References Cited

U.S. PATENT DOCUMENTS

| | | | |
|---|---|---|---|
| 3,145,237 | 8/1964 | Helden et al. | 260/670 |
| 3,401,207 | 9/1968 | Selwitz | 260/670 |
| 3,547,982 | 12/1970 | McKeon et al. | 560/254 |

OTHER PUBLICATIONS

Davidson et al., Chemistry and Industry, p. 457 (1966) and p. 1361 (1967).

*Primary Examiner*—Nicky Chan
*Attorney, Agent, or Firm*—Sherman & Shalloway

[57] ABSTRACT

The oxidative coupling of benzene or benzene derivatives to form the corresponding diphenyls, comprising contacting benzene or a benzene derivative, such as toluene, with molecular oxygen using as a catalyst β-diketo complexes of palladium such as acetylacetone-palladium complex. Use of at least one zirconium compound such as zirconium oxystearate in conjunction with the catalyst gives an increased catalytic activity. The diphenyls are intermediates for production of dyestuffs, pharmaceuticals and other chemicals, and also find application in the preparation of high-molecular-weight polyesters and polyamides.

6 Claims, No Drawings

PROCESS FOR PRODUCING DIPHENYLS

This is a continuation of Application Ser. No. 326,454 filed Jan. 24, 1973, which in turn is a continuation-in-part of Application Ser. No. 60,945 filed Aug. 4, 1970, both cases having been abandoned. This application is related to Application Ser. No. 326,523 filed Jan. 24, 1973, now U.S. Pat. No. 3,963,787 issued June 15, 1976, this patent also being a continuation-in-part of Application Ser. No. 60,945 filed Aug. 4, 1970 now abandoned.

This invention relates to a process for producing diphenyls by contacting benzene or benzene derivatives with molecular oxygen in a liquid phase thereby to dimerize them oxidatively. More specifically, the invention relates to a process for producing diphenyls wherein the oxidative coupling of benzene or benzene derivatives is carried out in the presence of a β-diketo complex of palladium as a catalyst.

The method of producing diphenyl compounds by dimerization of benzene or alkylbenzenes is interesting both scientifically and technologically.

The methods heretofore known include one wherein palladium chloride is reacted with an aromatic compound in the presence of an acid binder such as sodium acetate, or one wherein benzene or toluene is reacted with palladium acetate in acetic acid in the presence of an acid such as perchloric acid or sulfuric acid or an alkali salt such as sodium acetate or an alkaline earth metal.

In the method involving the use of palladium chloride and an acid binder, there are problems such as the corrosion of equipment by palladium chloride, and the production of acetate as by-product by the addition of an alkali salt such as sodium acetate as the acid binder. Expecially with alkylbenzenes, increased amounts of by-products such as benzylacetate pose a problem. Furthermore, the method involving the addition of perchloric acid or sulfuric acid also has the defect of corrosion of the equipment.

In the prior art processes described above, the palladium compound mainly acts as a reactant of stoichiometrical amount, and the palladium compound which has participated in the dimerization reaction is reduced to a low valency state. Thus, it does not have a high valency effective for the dimerization in the reaction system, and cannot act catalytically. In view of the fact that palladium is a very valuable metal, the prior art processes are not advantageous for the commercial production of diphenyl compounds from aromatic compounds, especially alkyl benzenes.

Accordingly, a primary object of the invention is to provide a process for producing diphenyls by the oxidative coupling of benzene or benzene derivatives using a palladium compound catalytically. The other objects and advantages of the invention will become apparent from the following description.

According to the present invention, benzene or a benzene derivative expressed by the following formula

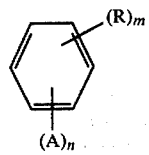

(1)

wherein
R's may be the same or different and represent an alkyl group having 1–4 carbon atoms;
m is a positive integer of 0 to 4;
A's may be the same or different and represent an alkoxy group having 1–4 carbon atoms or a halogen atom;
n is a positive integer of 0–2;
and the sume of m and n does not exceed 4, and when m is 0 or n is 0, $(R)_m$ or $-(A)_n$ respectively represents a hydrogen atom, is contacted with molecular oxygen, in the presence of at least one β-diketo complex of palladium as a catalyst, thereby to dimerize the benzene or a benzene derivative oxidatively to produce the corresponding diphenyl or a diphenyl derivative catalytically.

The compounds used as the starting material in the present invention may be any of the compounds that come within the formula (1) given above, and the specific examples are:

A. benzene;

B. monoalkyl benzenes such as toluene, ethylbenzene and isopropylbenzene;

C. dialkyl benzenes, for instnce, xylenes such as o-xylene and m-xylene, diethylbenzenes such as m-diethylbenzene or o-diethylbenzene, diisopropyl benzenes such as o-diisopropyl benzene and m-diisopropyl benzene, o—, m—, or p-ethyltoluene, o-, or p-isopropyltoluene;

D. trialkyl benzenes such as 1,2,3-trimethylbenzene, 1,2,4-trimethylbenzene, 1,3,5-trimethylbenzene, 1,2,4-triethylbenzene, 1,2-dimethyl-4-ethylbenzene, and 1,3-dimethyl-4-ethylbenzene;

E. monoalkoxybenzenes such as methoxybenzene (anisole), ethoxybenzene, n— or i-propoxybenzene, n— or i-butoxy benzene, and dialkoxybenzenes such as o—, m—, or p-dimethoxybenzene, and o—, m—, or p-diethylbenzene;

F. alkoxyalkyl benzenes such as o—, m—, or p-methoxy toluene, o—, m— or p-methoxy ethylbenzene, and o—, m— or p-ethoxytoluene;

G. halogenated benzenes such as monochlorobenzene, o—, m— or p-dichlorobenzene, monobromobenzene, o— or m-dibromobenzene, and o—, m— or p—monochloromonobromobenzene; and, H. o—, m— or p-monochlorotoluene, o—, m— or p—monobromobenzene, monochloroxylene, monobromo xylene, and o—, M— or p-methoxychlorobenzene.

As the starting materials of the present invention, those of the formula (1) wherein R is a lower alkyl group having 1 to 3 carbon atoms, m is 1, 2, or 3 and n is 0, or alkylbenzenes wherein m is 1 or 2 and which have one or two halogen atoms, especially chlorine atoms, as the $-(A)_n$ are preferred. Especially preferred starting materials are benzene, toluene, ortho- and/or meta-xylene.

The reaction by the process of the invention of oxidatively coupling the aforementioned starting materials is performed in a liquid phase either in the presence of absence of solvent using the palladium complex catalyst described below. When the reaction is carried out in the absence of a solvent, the reaction system is maintained liquid by the starting materials, and when it is carried out using a solvent, an organic liquid medium which is stable under the reaction conditions and inert to the reaction of the present invention is employed.

In the present invention, the oxidative coupling of the starting materials described above is carried out in the presence of a catalyst comprising at least one β-diketo complex of palladium.

The β-diketo complex of palladium that can be used in the invention mean the palladium complex having a keto and/or enol type β-diketo grouping as a ligand, the grouping being expressed by the following formula

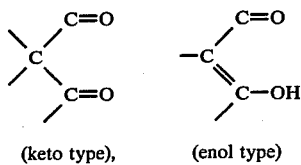

(keto type),   (enol type)

Examples of β-diketo complexes of palladium include, for instance, β-diketone complexes of palladium, β-ketoester complexes of palladium, and β-keto acid complexes of palladium. The β-diketo complexes of palladium are prepared by reacting palladium compounds capable of forming β-diketo complexes, such as organic carboxylates, a nitrate, perchlorate, chloride, oxide, or hydroxide of palladium with β-diketo grouping-containing compounds such as β-diketone, β-keto acid ester, β-keto acid or salts of these (the salts of an alkali metal such as sodium and potassium) which will be described hereinafter.

Examples of β-diketone include, for instance, acetylacetone, propionylacetone, butylacetone, isobutyrylacetone, caproylacetone, o-methylacetylacetone, tetraacetylethane, benzoylacetone, dibenzoylmethane, trifluoroacetylacetone, hexafluoroacetylacetone, benzyltrifluoroacetone, and β-naphthoyltrifluoroacetone. The β-keto acid esters include, for instance, acetoacetic acid ester, and trifluoroacetoacetic acid ester. As the β-keto acids, there can be named, for instance, acetoacetic acid, and trifluoroacetoacetic acid.

The details of these β-diketones, β-diketo acid and β-keto acid ester are described for example, in the following literature references, (a) Reinhold Publishing Corporation "The Chemistry of the Coordination Compounds" edited by John C. Bailar, JR.

(b) Prentice-Hall, Inc. "Chemistry of the Metal Chelate Compounds" by Arthur E. Martell and Melvin Caluin.

(c) The Chemical Society (London) "Stability Constants of Metal-Ion Complexes", Section I; Inorganic Ligands compiled by Lars Gunnar Sillen.

The aforementioned β-diketo complexes of palladium are not altogether necessary to add preformed β-diketo complexes of palladium, but the palladium compounds capable of forming the β-diketo complexes and the compounds containing a β-diketo grouping, such as β-diketones, β-keto esters or β-keto acids may be added to the reaction system of the present invention so as to form such β-diketo complexes of palladium.

The aforementioned β-diketo complexes of palladium may be used singly or in combination of two or more as the catalyst for the reaction of the invention. In the reaction system of the invention, a part of the β-diketo complex of palladium can be replaced by the organic carboxylate of palladium. In the process of the present invention, the palladium complex catalyst having a high valency effective for the reaction is reduced by the oxidative dimerization of the benzene, or its derivatives to a lower valency state, but is immediately oxidized and regenerated by the molecular oxygen present in the reaction system, thus maintaining a catalytic activity. Therefore, the palladium catalyst of the invention can be used even in very small amounts, and amount of the catalyst used in the invention is not particularly restricted. In general, the amount of the catalyst is at least $1 \times 10^{-5}$ gram-atom, calculated as metallic palladium, for each gram-mol of the benzene or its derivatives used on the starting material, particularly preferred being 0.001–0.1 gram-atom. The upper limit of the amount of the palladium catalyst used in the invention is determined by economic and other factors, and not critical by itself.

The aforementioned β-diketo complexes of palladium, when used conjointly with a zirconium compound, can give the intended diphenyls in high yields with an increased catalytic activity. An especially outstanding rise in catalytic activity is observed when the zirconium compound is added to the organic carboxylate of palladium.

Such zirconium compound may be any of those which are partially soluble in the reaction system of the present invention, and suitable examples include, for instance, (a) organic carboxylates of zirconium, (b) oxycarboxylates of zirconium, (c) halogen compounds of zirconium, and (d) oxyhalogen compounds of zirconium. The organic carboxylic acids which can provide carboxylic acid residues of the organic carboxylates of zirconium mentioned in (a) above, may include any of aliphatic carboxylic acids, alicyclic carboxylic acids and aromatic carboxylic acids; they may not only be monocarboxylic acids, but also dibasic or polybasic carboxylic acids. Examples of said organic carboxylic acids are:

(i) aliphatic monocarboxylates having 1–20 carbon atoms such as formate, acetate, trifluoroacetate, monochloroacetate, propionate, n— or iso-butyrate, laurate, palmitate, and stearate;

(ii) aliphatic carboxylates such as naphthenate, cyclohexanemonocarboxylate, and methyl cyclohexanemonocarboxylate; and (iii) benzenecarboxylates or naphthalenecarboxylates such as benzoate, o—, m—, or p-toluylate, phthalate, p-tertiary butylbenzoate, o—, m—, or p-methoxybenzoate, chlorobenzoate and naphthate.

These organic carboxylates of zirconium are prepared by using the organic carboxylic acids and inorganic compounds capable of forming the salts of zirconium, such as the hydroxide, nitrate, perchlorate, and oxide of zirconium, and other suitable organic compounds of zirconium. Examples of the preferred organic carboxylates of zirconium include formate, acetate, propionate, n— or iso-butyrate, benzoate, and naphthenate.

The acids capable of providing the oxycarboxylic acid residues of the oxycarboxylates of zirconium may be any of the aforementioned organic carboxylic acids having an oxy group. Suitable examples of the oxycarboxylic acids include oxyformic acid, oxyacetic acid, oxypropionic acid, oxy n— or oxy iso-butyric acid. These oxycarboxylates of zirconium can be prepared by the same salt-forming reaction as used in the preparation of the organic carboxylates mentioned above.

As the halogen compounds of zirconium under (c) above, any of the halides such as chloride, bromide, iodide, and fluoride of zirconium can be used, the chloride and bromide being preferred.

Examples of the oxyhalogen compounds of zirconium mentioned under (d) above include, for instance, oxychloride, oxybromide or oxyiodide of zirconium, and the oxychloride is preferred.

These zirconium compounds (a), (b), (c) and (d) may be formed in the reaction system of the present invention. These zirconium compounds can be present in the reaction system of the present invention either alone or in admixtures of two or more.

The amount of the zirconium compound used in the process of the present invention is not particularly restricted. But in general, it is 0.01–100 gram-atoms, preferably 0.1–50 gram-atoms, calculated as zirconium metal, per gram-atom of palladium of the palladium complex catalyst.

The catalyst comprising said palladium and zirconium may further contain compounds. of Pt, Rh, Ir, Au, or Ag, which are partically soluble in the reaction system of the present ivention, especially organic acid salts of these compounds or the oxides or hydroxides of these compounds which can form organic acid salts in an organic carboxylic acid solvent.

According to the process of the invention, the conjoint use of the zirconium compound makes it possible to cause palladium to act catalytically, and to obtain diphenyls in high yields.

As previously stated, an inert organic liquid medium may be present in the reaction system of the present invention. The amount of such medium is ususally not more than 100 times the weight of the benzene or benzene derivatives used as the starting material.

An inert liquid compounds preferably liquid which is liquid under the reaction condition of the invention, such as aliphatic hydrocarbons, halogenated hydrocarbons, esters, ketones and ethers, can also be used advantageously as the reaction medium. Specific examples of such inert liquid compound are:

(A) aliphatic hydrocarbons such as hexane, heptane and octane;

(B) alicyclic hydrocarbons such as cyclopentane and cyclohexane;

(C) chlorides and bromides of (A) or (B);

(D) aliphatic ethers or alicyclic ethers such as methyl ether, ethyl ether, propyl ether, cyclopentyl ether, and cyclohexyl ether;

(E) esters of aliphatic carboxylic acids such as methyl acetate, ethyl propionate and cyclohexyl acetate;

(F) aliphatic ketones or alicyclic ketones such as acetone, di-t-butyl ketone and dicyclohexyl ketone, and (G) organic carboxylic acids including aliphatic, alicyclic and aromatic carboxylic acids, such as acetic acid, propionic acid, n— or isobutyric acid, naphthenic acid and benzoic acid. Aqueous solutions of these carboxylic acids containing not more than 15% by weight of water can also be used as the reaction medium.

In the present invention, the oxidative coupling of the benzene or a benzene derivative can be carried out catalytically by contacting the benezene or benzene derivatives with molecular oxygen in a liquid phase in the presence of the aforementioned palladium complex catalyst or in the presence of said palladium complex catalyst and the aforesaid zirconium compound, thereby to obtain diphenyls corresponding to the starting materials. For ensuring a smooth proceeding of the oxidative coupling reaction of the present invention, it is preferable to heat the reaction system to a temperature of 100° to 300° C., especially 110° to 250° C. The reaction can proceed even at a temperature below 100° C. But it is preferable to carry out the reaction at a temperature of at least 100° C., and good results are obtained within the temperature range of 100° to 160° C.

The molecular oxygen used in the practice of the present invention may be pure oxygen or a gas containing molecular oxygen which is diluted with an inert gas such as nitrogen, argon, helium or carbon dioxide, an example being air. It is preferred that such molecular oxygen or molecular oxygen-containing gas should be contacted with the benzene or benzene derivatives at a pressure of at least 0.2, preferably at least 1 atmosphere, especially at least 2.5 atmosphere calculated as the partial pressure of oxygen. No specific upper limit is set on the partial pressure of oxygen in the molecular oxygen or molecular oxygen-containing gas. Too high a partial oxygen pressure, however, is commercially undesirable, and suitable pressures are generally below 300 atmospheres.

The process of the invention can be practised either by the batchwise, intermittent, continuous or circulating method. The wall of a reactor used in the invention may be of any materials which exhibit resistance to corrosion. If no solvent is used, the materials may be iron. Generally, however, stainless steel is suitable, and examples of other materials that can be used include Hastelloy B, Hastelloy C, silver, nickel, titanium, titanium alloy, tantalum, glass lining and fluorine resin lining.

The diphenyls obtained by the process of the invention are separated from the reaction mixture by such procedures as evaporation, distillation, filtration or centrifugation according to their physical characteristics, and can be purified by any means usually employed in the art.

According to the process of the invention, it is advantageous to separate diphenyls from the reaction mixture at a temperature of below 200° C., preferably below 180° C. By separating the diphenyls from the reaction mixture at these temperatures, the catalysts can still remain highly active in the residual reaction mixture. Hence, it is possible to use the catalysts in an active state contained in the residual reaction mixture with or without separation therefrom, and recycle them for further use. The separation of the active catalysts from the residual solvent can be effected by any known means such as extraction, recrystallization, sublimation and distillation under reduced pressure.

As previously stated, benzene or benzene derivatives can be converted to the corresponding diphenyls by a one-step catalytic reaction in accordance with the present invention, and a very small amount of the above-described palladium catalyst or the palladium-zirconium catalyst exhibits an effective catalytic activity in the reaction, giving the diphenyls in high yields and with high selectivities. The palladium or palladium-zirconium catalyst can be recovered, and recycled for further use.

The diphenyls obtained by the process of the invention can be used as intermediates for production of dyestuffs, pharmaceuticals and various other chemicals. Or after being converted to carboxylic acids or their esters, these diphenyls are used as the polybasic acid components in the synthesis of high molecular weight polyesters or polyamides or unsaturated polyesters.

The invention will further be described by the following Examples, which are intended to be illustrative rather than limitative. Unless otherwise specified, all parts in the Examples are parts by weight.

EXAMPLE 1

A stainless steel autoclave equipped with a stirrer was charged with 15 parts of toluene, and 0.287 part of palladium acetylacetonate, and the toluene was reacted for 4 hours at 130° C. with the introduction of oxygen at a partial pressure of 30 kg/cm$^2$G. Analysis of the resultant product indicated the formation of 3.20 parts of dimethyl diphenyl, which corresponded to 1868 mol % of the palladium acetylacetonate fed. This shows that the palladium salt acted catalytically. The recovered toluene weighed 11.1 parts, and the yield of dimethyl diphenyl based on the converted toluene was 83 %.

EXAMPLE 2

The procedure of Example 1 was repeated except that the reaction temperature was maintained at 100° C. There was obtained 0.97 part of dimethyl diphenyl, which corresponded to a yield of 566 mol % based on the palladium salt fed.

EXAMPLE 3

The procedure of Example 1 was repeated except that air was used as the oxygen-containing gas and the reaction pressure was maintained at 150 kg/cm$^2$G. There was obtained 3.00 parts of dimethyl diphenyl, which ocrresponded to a yield of 1750 mol % based on the palladium salt fed.

EXAMPLES 4 to 7

A stainless steel autoclave equipped with a stirrer was charged with each of the starting materials indicated in the following table and 0.287 part of palladium acetylacetonate, and the reaction of the starting material was performed for 4 hours at 125° C. with the introduction of oxygen at a partial pressure of 50 kg/cm$^2$G. The results obtained are shown in the following table.

| Example No. | Starting materials | Diphenyls produced | Mol % of the product based on the catalyst |
| --- | --- | --- | --- |
| 4 | Benzene 15 parts | Diphenyl 2.27 parts | 1620 |
| 5 | o-Xylene 20 parts | Tetramethyl diphenyl 2.02 parts | 1020 |
| 6 | m-Xylene 20 parts | Tetramethyl diphenyl 1.84 parts | 930 |
| 7 | Ethyl benzene 25 parts | Diethyl diphenyl 2.39 parts | 1210 |

EXAMPLE 8 to 10

A stainless steel autoclave equipped with a stirrer was charged with 20 parts of toluene and each of the palladium complexes indicated in the following table, and the toluene was reacted for 4 hours at 115° C. with the introduction of oxygen at a partial pressure of 25 kg/cm$^2$G.

| Ex. No. | Palladium complexes | Amount of dimethyl diphenyl produced | Mol % of the product based on the catalyst |
| --- | --- | --- | --- |
| 8 | Propionyl acetone (0.315 part) | 1.06 parts | 620 |
| 9 | Methyl acetoacetate (0.319 part) | 1.08 parts | 632 |
| 10 | Benzoyl acetone (0.405 part) | 0.908 part | 530 |

EXAMPLE 11 to 14

The procedure of Example 1 was repeated except that the reaction temperature was varied as indicated in the following table. The results obtained are shown in the following table.

| Example No. | Temp. (°C.) | Amount of dimethyl diphenyl produced(parts) | Yield based on converted toluene (%) | Mole % of the product based on the catalyst |
| --- | --- | --- | --- | --- |
| 11 | 100 | 0.368 | 84 | 215 |
| 12 | 120 | 2.108 | 80 | 1230 |
| 13 | 150 | 3.478 | 76 | 2030 |
| 14 | 160 | 3.74 | 60 | 2180 |

EXAMPLE 15 to 17

The procedure of Example 1 was repeated except that the partial pressure of oxygen was varied as indicated in the following table. The results are shown in the table.

| Example No. | Partial pressure of oxygen (kg/cm$^2$G) | Amount of the product (parts) | Yield based on converted toluene (%) | Mol % of the product based on the catalyst |
| --- | --- | --- | --- | --- |
| 15 | 1 | 0.254 | 62 | 148 |
| 16 | 5 | 0.737 | 73 | 430 |
| 17 | 15 | 1.131 | 81 | 660 |

EXAMPLE 18

A stainless steel autoclave equipped with a stirrer was charged with 20 parts of toluene, and 0.319 part of palladium acetoacetate, and the toluene was reacted for 4 hours at 115° C. with the introduction of oxygen at a partial pressure of 25 kg/cm$^2$G. Gas-chromatographic analysis of the product indicated the formation of 0.54 part of dimethyl diphenyl, which corresponded to 316 mol % of palladium acetoacetate fed. This shows that the palladium salt acted catalytically under these conditions.

EXAMPLE 19

A stainless steel autoclave equipped with a stirrer was charged with 15 parts of toluene, 0.287 part of palladium acetylacetone and 0.21 part of palladium acetate, and the toluene was reacted for 4 hours at 110° C. with the introduction of oxygen at a partial pressure of 30 kg/cm$^2$G. Analysis of the product indicated the formation of 1.67 parts of dimethyl diphenyl, which corresponded to 487 mol % based on the palladium salt fed. This shows that the palladium salt acted catalytically.

EXAMPLE 20

A stainless steel autoclave equipped with a stirrer was charged with 15 parts of toluene, 32 parts of glacial acetic acid, 0.287 part of palladium acetylacetonate and 2.105 parts of zirconium oxyacetate, and the toluene was reacted for 4 hours at 130° C. with the introduction of oxygen at a partial pressure of 60 kg/cm². There was obtained 2.00 parts of dimethyl diphenyl, which corresponded to 580% based on the palladium salt fed. This shows that the palladium salt acted catalytically under these conditions.

EXAMPLE 21

The procedure of Example 20 was repeated except that 15 parts of anisole was used instead of the toluene. There was obtained a dimerized product of an amount corresponding to 490 mol % based on the palladium acetate fed. This shows that the palladium salt acted catalytically.

EXAMPLE 22

A stainless steel autoclave equipped with a stirrer was charged with 15 parts of toluene and 0.287 part of palladium acetylacetonate, and the toluene was reacted for 4 hours at 170° C. with the introduction of air at a pressure of 150 kg/cm²G. The reaction product was transferred to a distillation apparatus, and unreacted toluene was removed by distillation at a bath temperature of 120° C. and at normal atmospheric pressure. Thereafter, the system was maintained at a pressure of 2 mmHg and the bath temperature was raised to 180° C. to remove dimethyl diphenyl by distillation. There was obtained 3.6 parts of dimethyl diphenyl.

There was hardly any dimethyl diphenyl in the catalyst residue. The recovered catalyst and 15 parts of toluene were charged into a stainless steel autoclave, and the reaction was performed for 2 hours at 130° C. and at an air pressure of 150 kg/cm²G. There was obtained 0.224 part of dimethyl diphenyl, which corresponded to 131 mol % based on the palladium acetylacetonate initially fed. This shows that the palladium salt acted catalytically.

EXAMPLE 23

A stainless steel autoclave equipped with a stirrer was charged with 15 parts of toluene and 0.287 part of palladium acetylacetonate, and the toluene was reacted for 4 hours at 130° C. with the introduction of oxygen at a partial pressure of 30 kg/cm²G. The product obtained was transferred to a distillation apparatus, and unreacted toluene was removed by distillation at a bath temperature of 120° C. and at normal atmospheric pressure. The system was maintained at 2 mmHg, and the bath temperature was maintained at 160° C. Distillation under reduced pressure gave 3.1 parts of dimethyl diphenyl.

The catalyst residue thus obtained hardly contained any dimethyl diphenyl. When 15 parts of toluene and the recovered catalyst were charged into a stainless steel autoclave and reacted under the same conditions as mentioned above, 2.9 parts of dimethyl diphenyl was obtained. The amount corresponded to a yield of 80 mol % based on the reacted toluene, which corresponded to 1693 mol % based on the palladium salt fed. This shows that the palladium salt acted catalytically.

Comparative Example 1

The procedure of Example 23 was repeated except that the bath temperature at the time of recovering the catalyst was changed to 210° C. and the catalyst thus recovered was used. Dimethyl diphenyl was not formed at all. This shows that the cartalyst thus recovered did not exhibit activity in the dimerization reaction of toluene.

EXAMPLE 24

A stainless steel autoclave equipped with a stirrer was charged with 20 parts of toluene and 0.315 part of propionile acetone palladium complex, and the toluene was reacted for 4 hours at 115° C. with the introduction of oxygen at a partial pressure of 25 kg/cm²G. The reaction product was transferred to a distillation apparatus. Unreacted toluene was removed by distillation at a bath temperature of 120° C. and at normal atmospheric pressure. Thereafter, the system was maintained at 2 mmHg, and the temperature of the bath was maintained at 160° C. There was obtained 1.0 part of dimethyl diphenyl.

The catalyst residue thus obtained was used as a catalyst, and 20 parts of toluene was reacted in the same manner as mentioned above. There was obtained 0.96 part of dimethyl diphenyl, which corresponded to 580 mol % of the palladium complex fed. This shows that the palladium complex acted catalytically.

EXAMPLE 25

A stainless steel autoclave equipped with a stirrer was charged with 20 parts of o-xylene and 0.287 part of palladium acetylacetonate, and the o-xylene was reacted for 4 hours at 125° C. with the introduction of oxygen at a partial pressure of 50 kg/cm²G. The reaction product obtained was transferred to a distillation apparatus, and unreacted toluene was removed by distillation at a bath temperature of 120° C., and normal atmospheric pressure. Thereafter, the temperature of the bath was raised to 150° C. and the system was maintained at 0.05 mmHg. Under these conditions, 20 parts of tetramethyl diphenyl was removed by distillation.

Using the catalyst residue so obtained, 20 parts of o-xylene was reacted under the same conditions as set forth above, thereby to form 1.95 parts of tetramethyl diphenyl. This corresponded to 985 mol % of the palladium complex fed. This shows that the palladium complex acted catalytically.

EXAMPLE 26

The catalyst recovered after removing unreacted toluene and dimethyl diphenyl by distillation in the procedure of Example 23 was recrystallized from toluene, and purified. In the same manner as set forth in Example 23, 15 parts of toluene was charged into a stainless steel autoclave together with the purified catalyst. The toluene was reacted for 4 hours at 130° C. with the introduction of oxygen at a partial pressure of 30 kg/cm²G. Dimethyl diphenyl was obtained in a yield of 82 mol % based on the reacted toluene, which corresponded to 1580 mol % based on the palladium catalyst fed.

EXAMPLE 27

The procedure of Example 23 was repeated, and the following results were obtained. It is seen from the results that the catalyst can be recovered and resued continuously.

| Number of catalyst recovering operations | Selectivity of dimethyl diphenyl based on reacted toluene(mol %) | Amount of dimethyl diphenyl produced (mol % based on the palladium fed) |
|---|---|---|
| 2 | 81 | 1650 |
| 3 | 78 | 1540 |

| Number of catalyst recovering operations | Selectivity of dimethyl diphenyl based on reacted toluene(mol %) | Amount of dimethyl diphenyl produced (mol % based on the palladium fed) |
|---|---|---|
| 4 | 77 | 1548 |

EXAMPLE 28

A stainless steel autoclave equipped with a stirrer was charged with 20 parts of toluene and 0.319 part of palladium methyl acetoacetate, and the toluene was reacted for 4 hours at 115° C. with the introduction of oxygen at a partial pressure of 25 kg/cm²G.

The reaction product was transferred to a distillation apparatus. Unreacted toluene was removed by distillation at 120° C. at normal atmospheric pressure, and dimethyl diphenyl was removed by distillation at 160° C. and 2 mmHg. There was obtained 1.00 part of dimethyl diphenyl. Using the catalyst recovered in the residue, 20 parts of toluene was oxidatively dimerized under the same conditions as set forth above. There was obtained 0.95 part of dimethyl diphenyl, which corresponded to 556 mol % based on the palladium salt fed.

EXAMPLES 29–33

These Examples illustrate the relation between the partial pressure of oxygen and the yield of diphenyls for easy understanding.

A stainless steel autoclave equipped with a stirrer was charged with 15 parts of toluene, and 0.287 part of palladium acetylacetonate, and the toluene was reacted for 4 hours at 130° C. with introduction of oxygen at a partial pressure indicated in the following table. The results obtained are known in the following table.

| Ex. No. | Oxygen partial pressure(kg/cm²) | Dimethyl diphenyl produced(part) | Mol % of the product based on the catalyst |
|---|---|---|---|
| 29 | 0.8 | 0.206 | 120 |
| 15 | 1.0 | 0.254 | 148 |
| 30 | 3.5 | 0.448 | 260 |
| 16 | 5.0 | 0.734 | 430 |
| 31 | 7.0 | 0.974 | 574 |
| 17 | 15.0 | 1.131 | 660 |
| 32 | 20.0 | 1.871 | 1088 |
| 1 | 30.0 | 3.20 | 1868 |
| 33 | 50.0 | 3.050 | 1773 |

EXAMPLE 34–41

These Examples also illustrate the relation between the partial pressure of oxygen and the yields of the diphenyls for easy understanding.

A stainless steel autoclave equipped with a stirrer was charged with 30 parts of toluene, and 0.202 parts bis-(benzoylacetonato)palladium (II) [Pd(CH₃COCH-COC₆H₅)₂], and the toluene was reacted for 6 hours at 150° C. with introduction of oxygen at a partial pressure indicated in the following table. The results obtained are shown in the following table.

| Ex. No. | Oxygen partial pressure(kg/cm²) | Dimethyl-diphenyl produced(part) | Mol % of the product based on the catalyst |
|---|---|---|---|
| 34 | 1.0 | 0.0959 | 111.3 |
| 35 | 2.5 | 0.0888 | 103.4 |
| 36 | 5.0 | 0.1119 | 130.2 |
| 37 | 8.0 | 0.2284 | 265.6 |
| 38 | 12.0 | 1.1081 | 1290.0 |
| 39 | 15.0 | 2.7550 | 3203.4 |
| 40 | 20.0 | 3.6090 | 4196.5 |
| 41 | 30.0 | 4.2120 | 4897.7 |

EXAMPLE 42

A stainless steel autoclave equipped with a stirrer was charged with 30 parts of toluene, and 0.259 part of Pd(C₆H₅COCHCOC₆H₅)₂, and the toluene was reacted for 6 hours at 150° C. with the introduction of oxygen at a partial pressure of 20 kg/cm²G. Analysis of the resultant product indicated the formation of 0.5910 part of dimethyldiphenyl, which corresponded to 687.2 mol % of the palladium complex fed.

EXAMPLE 43

A stainless steel autoclave equipped with a stirrer was charged with 30 parts of toluene, and 0.1946 part of Pd(CH₃COCHCOCH₃)₂, and the toluene was reacted for 6 hours at 150° C. with in introduction of oxygen at a partial pressure of 20 kg/cm²G. Analysis of the resultant product indicated the formation of 3.4188 parts of dimethyldiphenyl, which corresponded to 3975.3 mol % of the palladium complex fed.

We claim:

1. A process for producing diphenyls which comprises contacting benzene or a benzene derivative expressed by the following formula

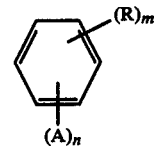

wherein
R's may be same or different and represent alkyl having 1 to 4 carbon atoms;
m is a positive integer of 0 to 4;
A's may be the same or different and represent alkoxy having 1 to 4 carbon atoms or a halogen atom;
n is a positive integer of 0 to 2; and
the sum of m and n does not exceed 4 and when m is 0 or n is 0, —(R)$_m$ or —(A)$_n$ respectively represents a hydrogen atom,
with molecular oxygen, in the absence of a solvent and in the presence of a β-diketo complex of palladium as a catalyst in an amount of 0.001 to 0.1 gram-atom calculated as metallic palladium, for each gram-mole of benzene or its derivative, thereby to dimerize the benzene or benzene derivative oxidatively wherein the oxidation coupling is carried out at a pressure of at least 2.5 atmospheres calculated as the partial pressure of oxygen at a temperature of 100° to 300° C.

2. The process of claim 1 wherein the reaction temperature is in the range of 100° C. to 160° C.

3. The process of claim 1 wherein the oxidative coupling is carried out at a temperature in the range of 110° to 250° C.

4. The process of claim 1 where R is a lower alkyl having 1 to 3 carbon atoms, m is 1, 2 or 3 and n is 0.

5. The process of claim 1 wherein m is 1 or 2, n is 1 or 2 and A is chlorine.

6. The process of claim 1 wherein said benzene or benzene derivative is selected from the group consisting of benzene, toluene, ortho-xylene and meta-xylene.

* * * * *